United States Patent [19]

Okazaki et al.

[11] Patent Number: 4,988,569
[45] Date of Patent: Jan. 29, 1991

[54] COMPLEX PHOSPHATE ADSORBENT OF MGO-TIO₂

[75] Inventors: Susumu Okazaki, Mito; Hiroshi Endo, Chofu; Kuniaki Hino, Tokyo, all of Japan

[73] Assignee: Kureha Kagaku Kogyo Kabushiki Kaisha, Tokyo, Japan

[21] Appl. No.: 235,415

[22] Filed: Aug. 24, 1988

[30] Foreign Application Priority Data

Aug. 25, 1987 [JP] Japan .................................. 62-210713
Aug. 25, 1987 [JP] Japan .................................. 62-210714

[51] Int. Cl.⁵ ........................... B32B 5/16; B01D 11/00
[52] U.S. Cl. ..................................... 428/403; 210/645; 210/646; 210/906; 424/400; 424/422; 424/490; 428/402.24; 502/416; 502/417; 502/425; 502/427; 502/439
[58] Field of Search .................... 502/8, 427, 439, 417, 502/416, 425; 428/403, 402.24; 210/645, 646, 906; 424/400, 422, 490

[56] References Cited

U.S. PATENT DOCUMENTS

| | | | |
|---|---|---|---|
| 2,523,875 | 9/1950 | Morrell et al. | 502/417 |
| 2,991,201 | 7/1961 | Joyce | 502/417 X |
| 3,876,451 | 4/1975 | Zall | 210/39 X |
| 4,125,482 | 11/1978 | Sinha | 502/417 |
| 4,242,226 | 12/1980 | Siren | 502/417 X |
| 4,247,393 | 1/1981 | Wallace | 210/638 |
| 4,248,736 | 2/1981 | Fuchigami et al. | 502/402 |
| 4,474,853 | 10/1984 | Watanabe | 428/403 |
| 4,537,873 | 8/1985 | Kato et al. | 502/256 X |
| 4,581,141 | 4/1986 | Ash | 210/648 |

FOREIGN PATENT DOCUMENTS 55-132635 10/1980 Japan .................................. 502/417

OTHER PUBLICATIONS

*Chemical Abstracts*, vol. 93, Sep. 1, 1980, p. 393, Abstract No. 101513v.
*Chemical Abstracts*, vol. 94, No. 12, Jun. 1981, p. 342, Abstract No. 197402c.
Patent Abstracts of Japan, vol. 10, No. 214(C-362) [2270], Jul. 25, 1986.

*Primary Examiner*—Thurman K. Page
*Attorney, Agent, or Firm*—Nixon & Vanderhye

[57] ABSTRACT

The present invention discloses a phosphate adsorbent comprising an MgO-TiO₂ complex as an active ingredient and a phosphate adsorbent having said complex deposited on active carbons. In the preferred embodiments of the present invention, the MgO/TiO₂ molar ratio in the complex is in the range of 99.99/0.01 to 80/20, the specific surface area of the adsorbent as measured by BET method is in the range of 50 to 700 m²/g. and the absorbent shows a crystal diffraction pattern of MgO in powder X-ray diffractometry. The phosphate adsorbent according to the present invention is useful as an antihyperphosphoremial agent, an adsorbent for hemoperfusion and a therapeutical agent for renal diseases.

13 Claims, 3 Drawing Sheets

Change of Phosphate Adsorption Capacity on Standing

Comparison of Phosphate Adsorption Capacity

COMPLEX PHOSPHATE ADSORBENT OF MGO-TIO₂

BACKGROUND OF THE INVENTION

The present invention relates to a phosphate adsorbent comprising an $MgO$-$TiO_2$ complex.

Patients suffering from functional disturbance in kidney or liver are increasing recently. These patients have a weak function to excrete waste metabolites out of a body system, so that such waste materials are accumulated in the system to cause various physiological troubles. Therefore, means and treatments for improving conditions of the patients suffering from such functional disturbance have been performed by removing such waste metabolites.

Chronic renal failure is a typical cases of functional disturbance of kidney. At present, methods such as hemocatharsis by a dialysis membrane and hemoperfusion by active carbons are applied for treatments of the renal failure.

The patients with chronic renal failure have weak renal function to excrete phosphate into urine. However, said hemocatharsis using a dialysis membrane is incapable of sufficiently controlling the phosphate concentration in blood and quite ineffective for the adsorption of phosphate in an intestinal tract. On the other hand, the adsorption method using active carbons has the problem that adsorptivity of inorganic substance such as phosphate is very poor comparing with adsorptivity of organic substance, due to the nature of active carbons.

Accordingly, the patients with chronic renal failure cannot avoid suffering from hyperphosphoremia as a complication. Conventionally, to prevent such complication, a phosphate binding agent of an aluminum compound, such as aluminum hydroxide or aluminum carbonate, has been administered to the patient. This type of phosphate binding agent, however, has little effect on the patient who takes a large amount of phosphorus (more than 1,500 mg/day) because of low phosphate adsorptivity of said binding agent. Further, administration of this type of binding agent in a large amount could develop adverse side effects such as constipation, nausea, vomitting, etc. Furthermore, it has been recently reported that aluminum accumulates in the patients with chronic renal failure to cause osteomalacia or encephalopathy.

On the other hand, a report has been made recently on the possible use of MgO alone as a phosphate adsorbent. Use of MgO alone, however, involves the serious problem that its storage and handling are very complicated and troublesome because MgO is susceptible to the presence of carbon dioxide in an atmosphere and when it is left there, its phosphate adsorptivity is reduced with time.

Further, there are several reports concerning phosphate adsorbents, such as U.S. Pat. No. 4,474,853 and Japanese Patent Application Laid-Open (KOKAI) Nos. 59-76,536 (1984) and 60-132,644 (1985). However, all these reports disclose zirconium compounds only as the adsorbent.

In view of these circumstances, the present inventors have studied extensively to provide an adsorbent which is highly safe in vivo, has excellent phosphate adsorbing characteristics and is capable of maintaining such characteristics for a long time and as a result have found that an $MgO$-$TiO_2$ complex, comprising a specific composition, has 7 to 8 times higher phosphate adsorptivity than the conventional aluminum hydroxide type adsorbents, is capable of maintaining high phosphate adsorptivity for a long time and is quite apposite to the object of this invention. Furthermore, the present inventors have found that an adsorbent having said $MgO$-$TiO_2$ complex deposited on an internal surface of active carbons shows a very excellent phosphate adsorptivity while maintaining inherent adsorbing characteristics of active carbons without being impaired.

SUMMARY OF THE INVENTION

An object of this invention is to provide a phosphate adsorbent which is highly safe even in vivo, has an excellent phosphate adsorptivity and can maintain its excellent adsorptivity for a long time.

Another object of this invention is to provide a phosphate adsorbent containing an $MgO$-$TiO_2$ complex as an active ingredient.

Still another object of this invention is to provide a phosphate adsorbent in which the $MgO/TiO_2$ molar ratio is in the range of 99.99/0.01 to 80/20 and the specific surface area as measured by BET method is 50 to 700 m²/g and which shows a crystal diffraction pattern of MgO when subjected to powder X-ray diffraction.

Yet another object of this invention is to provide a phosphate adsorbent having an $MgO$-$TiO_2$ complex deposited on active carbons so that said adsorbent has the inherent adsorbing characteristics of active carbons as well as the phosphate adsorptivity of said complex.

A further object of this invention is to provide a phosphate adsorbent having an $MgO$-$TiO_2$ complex deposited on spherical active carbons, having very few dust formation.

Still another object of this invention is to provide a therapeutic agent for renal diseases comprising an $MgO$-$TiO_2$ complex deposited on spherical active carbons having an average particle diameter of 0.1 to 1 mm, a specific surface area of 500 to 2,000 m²/g as measured by methanol adsorption method and a pore volume, having a radius of 100 to 75,000 Å, of 0.1 to 1.0 cm³/g, which agent, when administered orally, shows an excellent adsorptivity of waste metabolites represented by creatinine, causes no adverse side effects such as constipation and also has excellent phosphate adsorptivity.

An additional object of this invention is to provide an antihyperphosphoremial agent and an adsorbent for hemoperfusion, both of which are highly safe in use.

DETAILED DESCRIPTION OF THE INVENTION

Figure 1:
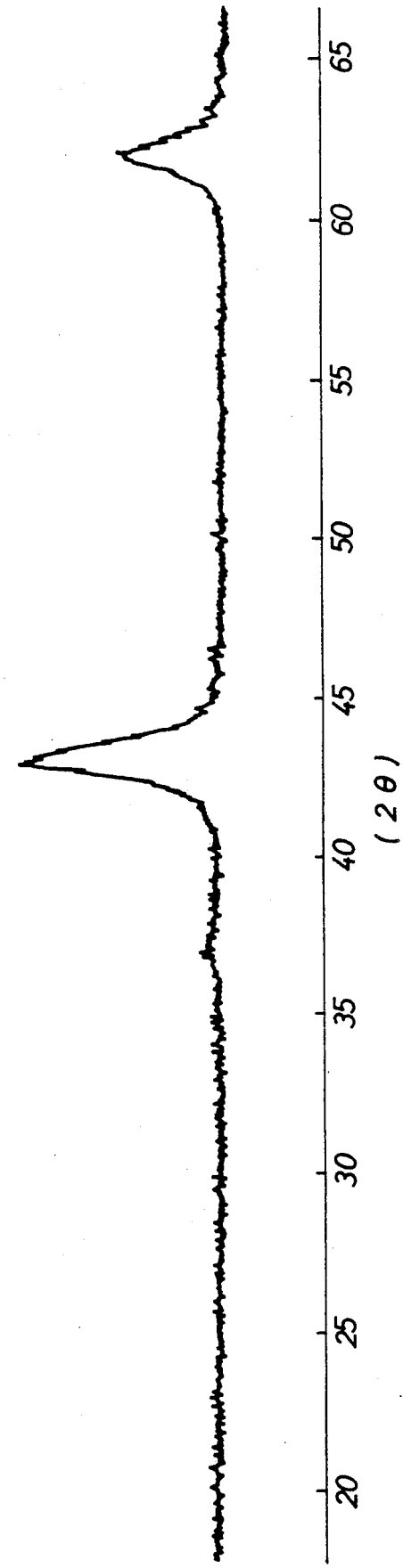
FIGS. 1 and 2 show the X-ray diffraction patterns of an $MgO$-$TiO_2$ complex according to the present invention and of a comparative adsorbent, respectively.

The phosphate adsorbent comprising an $MgO$-$TiO_2$ complex according to the present invention can be produced by mixing a magnesium compound and a titanium compound, hydrolyzing the mixture and calcining the resulting precipitate, or by mixing the metallic compounds and calcining the resulting mixture.

Various methods have been known to hydrolyze each of said metal compounds, but the preferable methods to hydrolyze metal compounds for the complex of the present invention comprise the following steps:

mixing an aqueous solution of magnesium salt and an aqueous solution of titanium salt and hydrolyzing the mixed solution with an aqueous solution of an alkali such as ammonia, or mixing alkoxides of said metals and hydrolyzing the mixture.

The object of calcination of precipitates on hydrolysis is not only complexing MgO and $TiO_2$ but also adjusting the characteristics, such as number of OH groups on the surface, chemical structure of the surface, specific surface area, etc., of the complex as a phosphate adsorbent. The calcination temperature is variable depending on the precipitate preparing method, adjusting conditions, blending ratio and other factors, but usually is preferable to perform at a temperature in a range of 200° to 1,000° C., more preferable 300° to 700° C. and specifically preferable 350° to 500° C. The calcination atmosphere is preferably free of water and carbon dioxide and an atmosphere of nitrogen is especially preferable for the calcination of the present invention.

Regarding the composition of the phosphate adsorbent according to the present invention, an $MgO/TiO_2$ molar ratio is in the range of 99.99/0.01 to 80/20, preferably 99.9/0.1 to 90/10, more preferably 99/1 to 95/5. The specific surface area of the complex, as measured by BET method, is preferably in the range of 50 to 700 $m^2/g$, more preferably 100 to 500 $m^2/g$.

In the $MgO$-$TiO_2$ complex, a small amount of $TiO_2$, which is one of the constituents of the complex, improves the phosphate adsorptivity, let alone a stability of the adsorptivity, as compared with single use of MgO, however, as the amount of $TiO_2$ in the complex increases, a disturbance in the crystal structure of MgO increases and when the molar ratio of $TiO_2$ exceeds 20%, the powder X-ray diffraction pattern specific to MgO crystal disappears and the phosphate adsorptivity of the complex is greatly reduced.

Also, when the molar ratio of $TiO_2$ in the complex is extremely small or when MgO alone is used, the resulting product is susceptible to the presence of carbon dioxide in an atmosphere and the adsorptivity reduces with a standing time.

The $MgO$-$TiO_2$ complex of the present invention, in which $TiO_2$ is present in a specified ratio, can maintain a stable phosphate adsorptivity for a long time even standing in an atmosphere containing carbon dioxide, as one of the excellent characteristics of the present adsorbent.

An adsorbent obtained by depositing an $MgO$-$TiO_2$ complex of the present invention on active carbons is also an embodiment within the scope of the claimed invention. This adsorbent is provided with both the organic substance adsorptivity inherent to active carbons and the stable phosphate adsorptivity of said complex and is very useful as an antihyperphosphoremial agent, an adsorbent for hemoperfusion or an orally administable therapeutic agent for renal diseases.

As active carbons for the present invention, there can be used granular carbon obtained by baking coconut charcoal or by binding powdery active carbons, but it is preferable to use spherical active carbons made of pitches or organic synthetic polymers as the starting material, because such spherical active carbons are substantially free from dust forming and is especially suitable as an adsorbent for hemoperfusion.

Such spherical active carbons can be manufactured by known methods such as disclosed in GB Patent No. 1,383,085 and U.S. Pat. Nos. 4,221,695, 4,371,454 and 4,420,443. As the starting materials for said spherical active carbons, there can be used, as pitches, petroleum and coal pitches and, as organic synthetic polymers, thermosetting resins such as phenol resin, epoxy resin, etc., or thermoplastic resins such as styrene resin, vinylidene chloride resin and their copolymer resins.

Among these spherical active carbons, especially preferred is the one having an average particle diameter of 0.1 to 1 mm, a specific surface area (measured by methanol adsorption method) of 500 to 2,000 $m^2/g$ and a pore volume, with a radius of 100 to 75,000 Å, of 0.1 to 1.0 $cm^3/g$, because this specified type of spherical active carbons shows an excellent adsorptivity of waste metabolites represented by creatinine and, when administered orally, causes no adverse side effects such as constipation which can be serious problems when ordinary active carbons are used.

The phosphate adsorbent of the present invention comprising the $MgO$-$TiO_2$ complex deposited on active carbons can be produced, for instance, in the following way.

Alkoxides of magnesium and titanium are mixed and dissolved in an aqueous solution of an acid, such as nitric acid, then active carbons are immersed in the solution, followed by hydrolysis with an aqueous solution of an alkali, such as ammonia or urea, to obtain an adsorbent precursor, and this precursor is calcined. The same calcining temperature as that of the complex can be applied and the calcination atmosphere free of water, carbon dioxide and oxygen is also preferable. Calcination in a nitrogen atmosphere is more preferable as in case of the complex preparation.

In the phosphate adsorbent of the present invention obtained by depositing an $MgO$-$TiO_2$ complex on active carbons (hereinafter referred to as "Mg-Ti-AC adsorbent"), it is preferable that the $MgO$-$TiO_2$ complex be deposited in an amount of 1 to 10% by weight. When the deposit is less than 1% by weight, no satisfactory effect on phosphate adsorption is obtained. When the deposite exceeds 10% by weight, a proportional increase of phosphate adsorptivity can not be expected and accordingly the use of said complex in excess of 10% by weight is meaningless.

The adsorbent of the present invention composed of an $MgO$-$TiO_2$ complex (hereinafter referred to as Mg-Ti adsorbent) is excellent in adsorption of phosphate. Further, in an acute toxicity test using Jcl-SD rats, the Mg-Ti adsorbent causes no abnormality in the test rats when administered orally even at a dose of 5,000 mg/kg.

Thus, the Mg-Ti adsorbent, either in its single form or in the form of a pharmaceutical composition, can be used as an antihyperphosphoremial agent. In this use, said adsorbent can also be made into a composition mixed with a pharmaceutically acceptable carrier and/or adjuvants and be offered in various forms, such as powder, granules, spherules, etc.

The available forms of pharmaceutical preparations of said adsorbent include tablet, sublingual tablet, pill, powder, granule, capsule, suppository, trouch, aqueous or oleaginous solution, suspension, emulsion, syrup, gell, etc. Tablet, powder, capsule, etc., can have enteric coating.

Although the pharmaceutically acceptable carriers usable in the composition of the present invention are not limited to the specific types; carriers such as water, gelatin, lactose, starch, pectin, magnesium stearate, stearic acid, talc, vegetable oils, gum arabic, polyalkylene glycol, vaseline, sorbitan trioleate, polyoxyethylene sorbitan monooleate, alkylphenols, aliphatic alcohols, polyvinyl pyrrolidone and the like can be exemplified, in general.

For the pharmaceutical preparations in the present invention, ordinary adjuvants such as sweetener, spice, coloring material, preservative, salt for adjusting osmotic pressure, buffering agent, etc. can be added according to necessity.

Although the content of the $MgO\text{-}TiO_2$ complex in the pharmaceutical compositions may be varied according to symptoms and other factors, it is usually 1 to 99% by weight, preferably 10 to 99% by weight. The pharmaceutical preparations can be administered either orally or per rectum. The dosage amount is variable depending on symptoms, etc., but it is usually 0.1 to 2 g per administration as $MgO\text{-}TiO_2$ complex, and the preparation may be administered one to three times a day. Generally, this can not be applied in case of emergency. In case of application to a patient of renal failures, the administration may be made either during pre-hemodialysis therapy or during hemodialysis therapy.

The Mg-Ti adsorbent, beside its use as an oral agent, can also be used as a phosphate adsorbent for hemoperfusion in a single form or in a coated form with a biocompatible substance such as heparin.

The Mg-Ti-AC adsorbent is not only capable of maintaining its stable adsorptivity of phosphorus compounds such as phosphoric acid ions but also has the adsorbing characteristics of active carbons, for example, an ability to remove the uremic organic metabolites, represented by creatinine. In other words, the Mg-Ti-AC adsorbent is not only useful for the treatment of hyperphosphoremia because of its adsorptivity of phosphorus compounds but can also be applied as an adsorbent for hemoperfusion as it has the ability to adsorb and remove the uremic metabolites such as creatinine.

The Mg-Ti-AC adsorbent can be coated with polymeric substances such as gelatin, albumin, poly(2-hydroxyethyl methacrylate) and the like. Also, it can be used in admixture with other types of adsorbent or in combination with other therapeutic treatment such as hemodialysis. Further, it can be used as an oral agent singly or in a form of a pharmaceutical composition for the purpose of removing phosphorus compounds, creatinine, etc., in a digestive tracts.

When the Mg-Ti-AC adsorbent is used in a form of tablet, capsule or the like, it can also be applied as an enteric agent.

The Mg-Ti-AC adsorbent of this invention prepared by depositing, for instance, 8.9% by weight of $MgO\text{-}TiO_2$ complex on active carbons caused no abnormality on the test animals in an acute toxicity test in which said adsorbent was orally administered to Jcl-SD rats at a dose of 15,000 mg/kg.

The content of the Mg-Ti-AC adsorbent in pharmaceutical compositions is subject to change according to symptoms of the disease, but it is preferably in the range of 50 to 99% by weight, more preferably 70 to 99% by weight.

Although the dose is also variable depending on symptoms of the disease, usually it is 0.5 to 10 g per administration as active carbons deposited with the complex, and the agent is preferably given to the patient one to three times a day. This, however, shall not necessarily be applied in the event of emergency. Further, the time of administration can be either during a pre-hemodialysis therapy or a hemodialysis therapy The present invention will hereinafter be described more in detail with reference to the non-limitative examples thereof.

EXAMPLE 1

0.57 g of titanium tetraisopropoxide, $[(CH_3)_2CHO]_4Ti$, was added dropwise into water under stirring and 1.2 g of nitric acid (61 wt %) was added. To this solution was added an aqueous solution of 51.3 g of magnesium nitrate, $Mg(NO_3)_2.6H_2O$, dissolved in 50 ml of water, followed by gradual addition of 30 g of 28% aqueous solution of ammonia to perform hydrolysis and the produced precipitate was separated by centrifugation. The obtained precipitate was washed well with water, heated up to 400° C. at a rate of 200° C./hr under a nitrogen flow and maintained at 400° C. for one hour to obtain 7.0 g of a $MgO\text{-}TiO_2$ complex ($MgO/TiO_2$ molar ratio=99/1).

A powder X-ray diffraction pattern of the $MgO\text{-}TiO_2$ complex obtained is shown in FIG. 1.

EXAMPLE 2

5.7 g of titanium tetraisopropoxide, $[(CH_3)_2CHO]_4Ti$, was added dropwise into water under stirring and then 12.4 g of nitric acid (61 wt %) was added thereto. To the solution was added an aqueous solution of 46.2 g of magnesium nitrate, $Mg(NO_3)_2.6H_2O$, dissolved in 50 ml of water, followed by gradual addition of 29 g of 28% aqueous solution of ammonia to perform hydrolysis and the produced precipitate was separated by centrifugation. The precipitate was washed well with water, heated up to 400° C. at a rate of 200° C./hr under a nitrogen flow and maintained at 400° C. for one hour to obtain 7.3 g of an $MgO\text{-}TiO_2$ complex ($MgO/TiO_2$ molar ratio=90/10).

COMPARATIVE EXAMPLE 1

Figure 2:
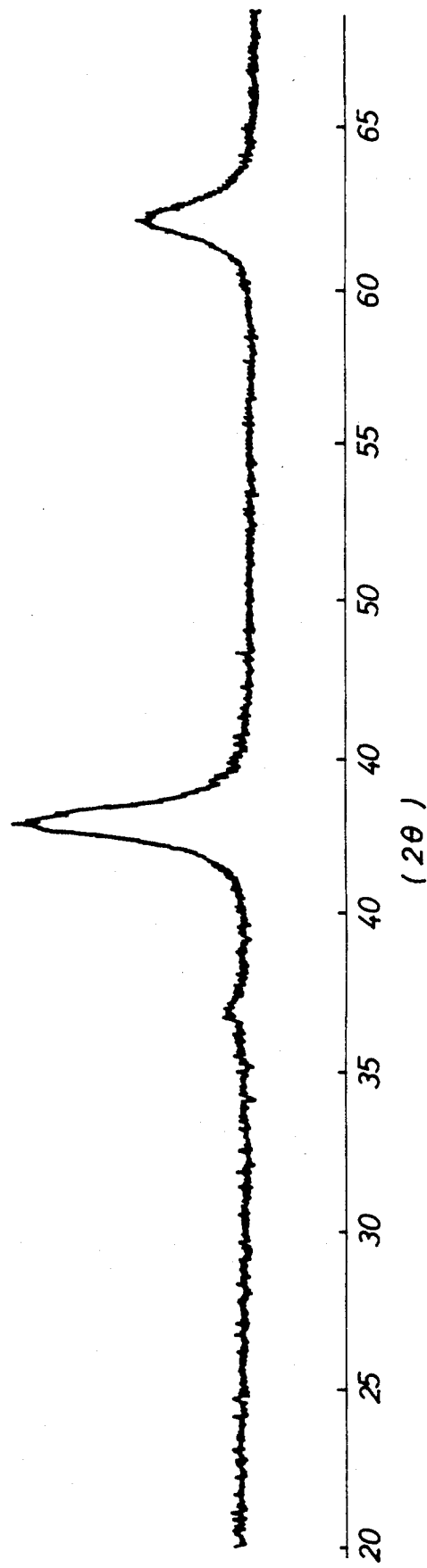

To an aqueous solution of 51.3 g of magnesium nitrate, $Mg(NO_3)_2.6H_2O$, dissolved in 50 ml of water was gradually added 29 g of 28% aqueous solution of ammonia to perform hydrolysis and the produced precipitate was separated with centrifugation. The precipitate was washed well with water, heated up to 400° C. at a rate of 200° C./hr under a nitrogen flow and maintained at 400° C. for one hour to obtain 6.4 g of magnesium oxide. A powder X-ray diffraction pattern of this product is shown in FIG. 2.

EXAMPLE 3

The specific surface area (measured by BET method) and powder X-ray diffraction of the specimens obtained in Examples 1 and 2 and Comparative Example 1 were determined. The results are shown in Table 1.

TABLE 1

| Item | Characteristics of the specimen | | |
| --- | --- | --- | --- |
| | Example 1 | Example 2 | Example 3 |
| Specific Surface Area (m²/g) | 220 | 350 | 120 |
| Crystal Diffraction Pattern of | Present | Present | Present |

TABLE 1-continued

| | Characteristics of the specimen | | |
|---|---|---|---|
| Item | Example 1 | Example 2 | Example 3 |
| MgO*[1] | | | |

*[1]Measured by X-ray diffractometry.

EXAMPLE 4

Model rats of renal failure are prepared by partially ligating a branch of left renal artery of Jcl-SD rats (11-week-old) first and 7 days after the first ligating, by ligating the hilum of right kidney. After 30 days of observation on 4 model rats, blood was drawn from the tail vein of each rat and from the time when creatinine and phosphate concentrations in the serum have reached 1.7±0.3 mg/dl and 7.1±0.3 mg/dl (as P concentration), respectively, the rats were allowed to take freely for 5 days a diet prepared by mixing 0.1% of the specimen of Example 1 with a standard diet (CE-2, manufactured by NIHON KUREA). After the feeding is over, blood was drawn from tail vein of each rat and phosphate concentration in the serum was measured. The results are shown in Table 2.

Measuring Devices:
Creatinine: measured by Beckman Creatinine Analyzer (Manufactured by Beckman & Inc.).
Phosphate: measured by RaBA-Mark II (Manufactured by KYOTO DAIICHI KAGAKU Co., Ltd.).

TABLE 2

| Antihyperphosphoremial Agent | | |
|---|---|---|
| | Phosphate Concentration (asP) in Serum (mg/dl) | |
| Dose of MgO—TiO$_2$ Complex of Example 1 (mg/day/rat) | Before Administration | After Administration |
| 13.9 ± 1.8 | 7.1 ± 0.3 | 5.8 ± 0.5 |

EXAMPLE 5

Figure 3:
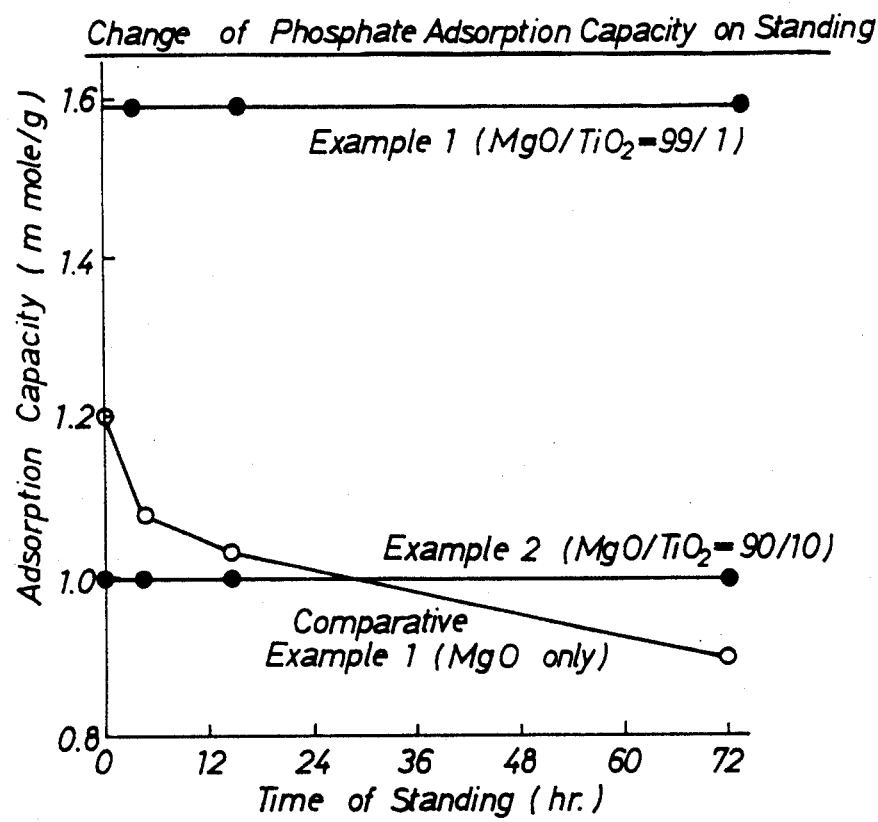
FIG. 3 shows the change with time of phosphate adsorptivity of the $MgO$-$TiO_2$ complex according to the present invention and of the comparative adsorbent.

Using the specimens obtained in Examples 1 and 2 and Comparative Example 1, change of phosphate adsorptivity of the specimens with time when they were left in the air was studied. The results are shown in FIG. 3. In the specimen of Comparative Example 1, which is MgO alone, the phosphate adsorptivity was reduced with time, whereas with the specimens of MgO-TiO$_2$ complexes obtained in Examples 1 and 2 any change of adsorptivity with time was not observed and could maintain stable adsorptivity.

When the time left in the air is zero, the phosphate adsorptivity of said complexes is higher than the single MgO when MgO/TiO$_2$ molar ratio is 99/1, but slightly lower when the MgO/TiO$_2$ molar ratio was 90/10. This indicates that the phosphate adsorptivity of the complexes reaches the peak when the MgO/TiO$_2$ molar ratio is around 99/1.

The phosphate adsorptivity was measured by putting 50 ml of a solution of sodium dihydrogenphosphate, NaH$_2$PO$_4$, with a concentration of 3.22 m mol/l into a triangle flask with a ground stopper, adding thereto 100 mg of specimen, shaking the flask at room temperature for 2 hours, filtering the solution and measuring the phosphate concentration in the filtrate by RaBA Ace.

EXAMPLE 6

Figure 4:
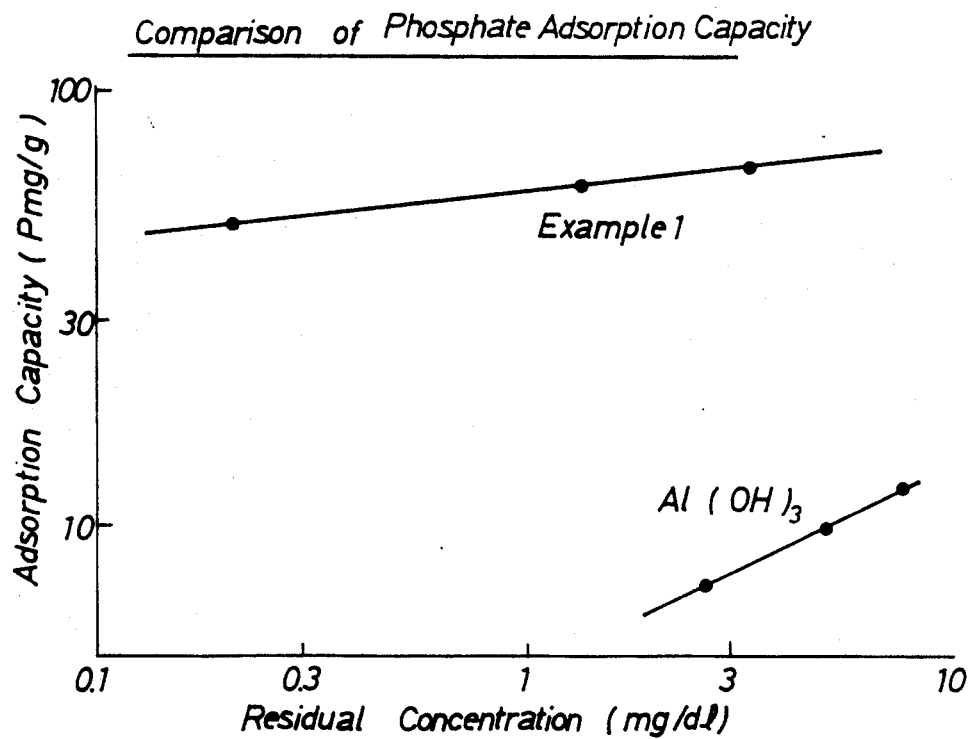
FIG. 4 shows a comparison of phosphate adsorptivities of the adsorbents between the present invention and the comparative example.

The phosphate adsorptivity of the MgO-TiO$_2$ complex obtained in Example 1 (MgO/TiO$_2$ molar ratio=99/1) and that of aluminum hydroxide were compared. The measurement of phosphate adsorptivity was conducted by the same procedure as used in Example 5. The amount of each specimen added was changed and the adsorption isotherms were prepared. The results are shown in FIG. 4. As seen from the figure, the MgO-TiO$_2$ complex shows 7 to 8 times higher phosphate adsorptivity than aluminum hydroxide.

Preparation of Spherical Active Carbons

A pitch obtained by crude oil cracking and an organic solvent compatible with the pitch were mixed, and the mixture was melted and dispersed in water containing a suspending medium. The organic solvent was removed from the obtained spherical particles and the spherical particles of pitch were infusibilized, carbonized and activated at 900° C. to obtain spherical active carbons having an average particle diameter of 0.4 mm, a specific surface area (measured by methanol adsorption method) of 1,200 m$^2$/g, and a pore volume (measured by mercury porosimetry) at a radius of 100 to 75,000 Å, of 0.3 cm$^3$/g.

EXAMPLE 7

0.22 g of titanium tetraisopropoxide [(CH$_3$)$_2$CHO]$_4$Ti, was added into water under stirring, and the precipitate was filtered, washed well with water, dispersed in 2 ml of water, and made a solution by adding 0.52 g of nitric acid (61 wt %). To the solution was added an aqueous solution of 20 g of magnesium nitrate, Mg(NO$_3$)$_2$.6H$_2$O, dissolved in 9 ml of water to prepare a magnesium/titanium mixed solution. 10 g of spherical active carbons produced as described above was added to the mixed solution and stirred at 50° C. for 2 hours.

The spherical active carbons were filtered out, dried at 80° C. for 4 hours and charged into 50 ml of 20% aqueous solution of ammonia and was stirred for 6 hours. Then the spherical active carbons were filtered out again, washed well with water, heated up to 400° C. at a rate of 200° C./hr in a nitrogen flow, maintained at 400° C. for one hour, and cooled. 10.89 g of adsorbent were obtained, which consists of the spherical active carbons with 8.9 wt % of an MgO-TiO$_2$ complex (MgO/TiO$_2$ molar ratio=99/1) deposited thereon.

EXAMPLE 8

8 ml of water was added to the magnesium/titanium mixed solution prepared in Example 7 and 10 g of spherical active carbons produced as described above were added to the solution and stirred at 50° C. for 2 hours. The spherical active carbons were filtered out, dried at 80° C. for 4 hours, then supplied into 50 ml of 20% aqueous solution of ammonia and stirred for 6 hours. From this solution, the spherical active carbons were filtered out, washed well with water, heated up to 400° C. at a rate of 200° C./hr in a nitrogen flow, maintained at 400° C. for one hour, then cooled. 10.66 g of adsorbent were obtained, which consists of the spherical active carbons with 6.6% of an MgO-TiO$_2$ complex (MgO/TiO$_2$ molar ratio=99/1) deposited thereon.

EXAMPLE 9

23 ml of water was added to the magnesium/titanium mixed solution prepared in Example 7, followed by addition of 10 g of spherical active carbons produced by the above-described method and by 2-hour stirring at 50° C. The spherical active carbons were filtered out, dried at 80° C. for 4 hours, supplied into 50 ml of 20% aqueous solution of ammonia and stirred for 6 hours. Then the spherical active carbons were filtered out, washed well with water, heated up to 400° C. at a rate of 200° C./hr in a nitrogen flow, maintained at 400° C. for one hour, then cooled. 10.47 g of adsorbent were obtained, which consists of the spherical active carbons with 4.7% of an MgO-TiO$_2$ complex (MgO/TiO$_2$ molar ratio=99/1) deposited thereon.

EXAMPLE 10

NaH$_2$PO$_4$.2H$_2$O was added to human serum to adjust its phosphate concentration to 10.1 mg/dl (as P concentration), and creatinine was further added thereto to have a creatinine concentration of 9.8 mg/dl. 10 ml of said serum were put into triangle flasks with ground stoppers, and then each 0.5 g of the adsorbents obtained in Examples 7 to 9 (comprising active carbons with an MgO-TiO$_2$ complex deposited thereon) and 0.5 g of spherical active carbons produced by the method described above were charged into the respective flask, followed by shaking at 37° C. for 2 hours. The supernatant serum was collected and the phosphate concentration and creatinine concentration were measured by RaBA-Mark II and Beckman Creatinine Analyzer, respectively. The results are shown in Table 3.

EXAMPLE 11

The adsorbent obtained in Example 7 having an MgO-TiO$_2$ complex deposited on active carbons was left in an air and the change of adsorptivity with time was measured by the same method as used in Example 10, provided that the initial phosphate and creatinine concentrations of the solution is 10.3 mg/dl (as P concentration) and 10.7 mg/dl, respectively. The results are shown in Table 4. Regarding the residual concentrations of phosphate and creatinine, no change with time was observed.

TABLE 3

| Adsorbent Obtained in the Following Example | Residual Concentration | |
|---|---|---|
| | Phosphate asP (mg/dl) | Creatinine (mg/dl) |
| Example 7 | 2.2 | 0.4 |
| Example 8 | 3.0 | 0.5 |
| Example 9 | 4.3 | 0.3 |
| Control *[1] | 9.7 | 0.3 |

*[1]Spherical Active Carbons with no complex deposited.

TABLE 4

| Time Left in an Air(hour) Substance Measured | 0 | | 72 | |
|---|---|---|---|---|
| | Phosphate | Creatinine asP | Phosphate | Creatinine asP |
| (mg/dl)*[1] | 2.3 | 0.3 | 2.0 | 0.4 |

*[1]Residual concentration of the substances.

What is claimed is:

1. A phosphate adsorbent comprising an MgO-TiO$_2$ complex as an active ingredient in which the MgO/TiO$_2$ molar ratio of said complex is 99.99/0.01 to 80/20.

2. The phosphate adsorbent according to claim 1, wherein the specific surface area of said complex of 50 to 700 m$^2$/g.

3. The phosphate adsorbent according to claim 1, wherein said complex shows a crystal diffraction pattern of MgO when subjected to powder X-ray diffractometry.

4. The phosphate adsorbent according to claim 1, wherein said complex is deposited on active carbons.

5. The phosphate adsorbent according to claim 4, wherein the amount of the said complex deposited on active carbons is 1 to 10% by weight.

6. A method of of treating hyperphosphoremia comprising administering to a person in need of same an antihyperphosphoremial-effective amount of a phosphate adsorbent comprising an MgO-TiO$_2$ complex in which the MgO-TiO$_2$ molar ratio of said complex is 99.99/0.01 to 80/20.

7. A method for adsorbing and removing phosphate from blood comprising contacting a patient's blood with a phosphate adsorbent comprising an MgO-TiO$_2$ complex in which the MgO/TiO$_2$ molar ratio of said complex is 99.99/0.01 to 80/20.

8. An antihyperphosphoremial agent containing the phosphate adsorbent of claim 1, in an amount effective for the treatment of hyperphosphoremia.

9. The antihyperphosphoremial agent containing the phosphate adsorbent of claim 1 for use as an adsorbent for hemoperfusion.

10. An adsorbent for hemoperfusion containing the phosphate adsorbent of claim 1, in an amount effective for reducing phosphate in perfusion blood.

11. The antihyperphosphoremial agent according to claim 8, in an orally administerable form.

12. A pharmaceutical composition comprising an MgO-TiO$_2$ complex in which the MgO/TiO$_2$ ratio is 99.99/0.01 to 80/20 together with a pharmaceutically acceptable carrier or diluent.

13. The phosphate adsorbent according to claim 4, in orally administerable form for the treatment of renal diseases.

* * * * *

UNITED STATES PATENT AND TRADEMARK OFFICE
CERTIFICATE OF CORRECTION

PATENT NO. : 4,988,569
DATED : January 29, 1991
INVENTOR(S) : OKAZAKI et al

It is certified that error appears in the above-identified patent and that said Letters Patent is hereby corrected as shown below:

Column 10, Claim 2, line 2, delete "of" (second occurrence) and insert --is--.

Column 10, Claim 6, line 1, delete "ofof" and insert --of--.

Signed and Sealed this

Fourth Day of May, 1993

Attest:

MICHAEL K. KIRK

Attesting Officer

Acting Commissioner of Patents and Trademarks